US012419528B2

(12) United States Patent
Loh

(10) Patent No.: US 12,419,528 B2
(45) Date of Patent: Sep. 23, 2025

(54) PHOTOPLETHYSMOGRAPHY-BASED BLOOD PRESSURE MONITORING DEVICE

(71) Applicant: Jeffrey Thomas Loh, Honolulu, HI (US)

(72) Inventor: Jeffrey Thomas Loh, Honolulu, HI (US)

(73) Assignee: KL Technologies LLC, Honolulu, HI (US)

( * ) Notice: Subject to any disclaimer, the term of this patent is extended or adjusted under 35 U.S.C. 154(b) by 269 days.

(21) Appl. No.: 18/097,269

(22) Filed: Jan. 15, 2023

(65) Prior Publication Data
US 2023/0293026 A1 Sep. 21, 2023

Related U.S. Application Data

(60) Provisional application No. 63/301,106, filed on Jan. 20, 2022.

(51) Int. Cl.
*A61B 5/021* (2006.01)
*A61B 5/00* (2006.01)

(52) U.S. Cl.
CPC .......... *A61B 5/02108* (2013.01); *A61B 5/681* (2013.01)

(58) Field of Classification Search
CPC . A61B 5/02416; A61B 5/02438; A61B 5/681; A61B 5/024; A61B 8/02; A61B 5/021; A61B 5/02108
See application file for complete search history.

(56) References Cited

U.S. PATENT DOCUMENTS

| 10,722,131 | B2 | 7/2020 | Banet et al. |
| 10,772,512 | B2 | 9/2020 | Klaassen et al. |
| 11,850,071 | B1 * | 12/2023 | Coakley ................ A61B 5/332 |
| 2016/0378069 | A1 * | 12/2016 | Rothkopf ................ G06F 3/016 |
| | | | 368/10 |
| 2017/0209055 | A1 * | 7/2017 | Pantelopoulos ..... A61B 5/7203 |
| 2017/0215749 | A1 | 8/2017 | Zhuo et al. |
| 2017/0340209 | A1 * | 11/2017 | Klaassen ................ A61B 5/021 |
| 2018/0028106 | A1 | 2/2018 | Leschinsky |

(Continued)

FOREIGN PATENT DOCUMENTS

WO WO-2021046237 A1 * 3/2021 .......... A61B 5/0077
WO 2021064213 A1 4/2021

OTHER PUBLICATIONS

International Search Report and Written Opinion by ISA/US of PCT/US24/28250, dated Aug. 14, 2024.

(Continued)

*Primary Examiner* — Gerald Johnson
(74) *Attorney, Agent, or Firm* — Batt IP A Law Corporation; Richard Batt

(57) ABSTRACT

A blood pressure monitoring device includes a wrist strap, a case, and a display. The strap portion is adapted to fasten the device to the wrist without occluding blood flow. At least one sensor modality is arranged within the case for obtaining sensor data from an artery in the wrist. In a preferred embodiment photoplethysmography sensors are incorporated in the case to generate PPG waveform data. A processor within the case is operable to compute mean arterial pressure, and optionally diastolic and systolic blood pressure based on extracted and computed features of the sensor data. Related methods and systems are also described.

32 Claims, 8 Drawing Sheets

(56) References Cited

U.S. PATENT DOCUMENTS

| | | |
|---|---|---|
| 2018/0156660 A1* | 6/2018 | Turgeon ................. G01J 1/44 |
| 2019/0021616 A1* | 1/2019 | Day ................. A61B 5/02427 |
| 2019/0076032 A1* | 3/2019 | Park ..................... A61B 5/681 |
| 2020/0397311 A1 | 12/2020 | Jung et al. |
| 2021/0067618 A1* | 3/2021 | Hong ................. A61B 5/6898 |
| 2021/0275043 A1 | 9/2021 | Ahmad et al. |
| 2022/0225885 A1 | 7/2022 | Loh |
| 2022/0400960 A1 | 12/2022 | Montgomery et al. |

OTHER PUBLICATIONS

Jonas Adler et al., "Solving ill-posed inverse problems using iterative deep neural networks", Inverse Problems, vol. 33, Issue 12, (2017).

Mukkamala et al., Toward Ubiquitous Blood Pressure Monitoring via Pulse Transit Time: Theory and Practice. IEEE Trans Biomed Eng. Aug. 2015; 62 (8):1879-901.

PCT/US23/60701 Application International Search Report and Written Opinion by ISA/US, mailed Jul. 23, 2023.

* cited by examiner

PHOTOPLETHYSMOGRAPHY-BASED BLOOD PRESSURE MONITORING DEVICE

CROSS-REFERENCE TO RELATED APPLICATIONS

This application claims priority to provisional application No. 63/301,106, filed Jan. 20, 2022, entitled PHOTOPLETHYSMOGRAPHY-BASED BLOOD PRESSURE MONITORING DEVICE", incorporated herein by reference in its entirety for all purposes.

BACKGROUND OF THE INVENTION

The invention relates to blood pressure measurement, and more particularly, to non-invasively non-compressive measurement of mean arterial pressure.

Mean arterial pressure (MAP) is the average blood pressure in an individual during a single cardiac cycle. MAP is considered to be the perfusion pressure seen by organs in the body. If the MAP is low for a substantial time, the vital organs will not get enough oxygen.

MAP can be measured directly by invasive monitoring by, for example, use of an intravascular pressure transducer. However, an intravascular device may cause problems, such as, embolization, nerve damage, infection, bleeding and/or vessel wall damage. Additionally, the implantation of an intravascular lead requires a highly skilled physician such as a surgeon, electrophysiologist, or interventional cardiologist.

Additionally, at normal resting heart rates, MAP can be approximated by measuring the systolic blood pressure (SBP) and diastolic blood pressure (DBP) and applying a formula in which the lower (diastolic) blood pressure is doubled and added to the higher (systolic) blood pressure and that composite sum then is divided by 3, or.

$$[1] MAP \approx (2 \times DBP + SBP)/3$$

The SBP and DBP can be measured with traditional blood pressure cuff devices. However, such devices are undesirable because the blood vessels are occluded. Additionally, due to the occluding nature of these types of devices, they are not wearable for any extended period of time. Thus, cuff-based devices do not serve well for continuous blood pressure monitoring.

There have been attempts to measure blood pressure without a cuff through use of pulse arrival time (PAT) and pulse transit time (PTT). Both PAT and PTT measure the time delay of a pulse launched from the heart to the finger, and has been shown to correlate to both systolic and diastolic blood pressures. See. E.g., Mukkamala et al., Ubiquitous Blood Pressure Monitoring via Pulse Transit Time: Theory and Practice. IEEE Trans Biomed Eng. 2015 August; 62(8): 1879-901. See also U.S. Pat. No. 10,722,131 to Banet.

Pulse arrival time (PAT) and pulse transit time (PTT) are typically measured with a conventional vital signs monitor that includes separate modules to determine both an electrocardiogram (ECG) and a value for pulse oximetry or oxygen saturation (SpO2). To obtain the ECG value, multiple electrodes are typically attached to a patient's chest to determine a time-dependent component of the ECG waveform characterized by a sharp spike called the 'QRS complex'. The QRS complex indicates an initial depolarization of ventricles within the heart and, informally, marks the beginning of the heartbeat and a pressure pulse that follows.

To obtain the SpO2, a bandage or clothespin-shaped sensor is attached to the patient's finger, and includes optical systems operating in spectral regions specific to detecting and quantifying the amount of hemoglobin in the underlying artery. The optical module typically includes first and second light sources (e.g., light-emitting diodes, or LEDs) that transmit optical radiation at, respectively, red ($\lambda$-600-700 nm) and infrared ($\lambda$-800-1200 nm) wavelengths.

A photodetector measures radiation emitted from the optical systems that transmits through the patient's finger. Other body sites, e.g., the ear, forehead, and nose, can also be used in place of the finger. During a measurement, a microprocessor analyses both red and infrared radiation measured by the photodetector to determine time-dependent waveforms corresponding to the different wavelengths, each called a photoplethysmogram waveform (PPG). The PPG shows for each heartbeat the variation in volume of arterial blood, based on the amount of radiation absorbed along the path of light between the LEDs and the photodetector. A SpO2 value can be calculated from the PPG waveforms. Time-dependent features of the PPG waveform indicate both pulse rate and a volumetric absorbance change in an underlying artery (e.g., in the finger) caused by the propagating pressure pulse.

Typical PAT measurements determine the time separating a maximum point on the QRS complex (indicating the peak of ventricular depolarization) and a portion of the PPG waveform (indicating the arrival of the pressure pulse). PAT depends primarily on arterial compliance, the propagation distance of the pressure pulse (which is closely approximated by the patient's arm length), and blood pressure. To account for patient-specific properties, such as arterial compliance, PAT-based measurements of blood pressure are typically 'calibrated' using a conventional blood pressure cuff. Typically, during the calibration process the blood pressure cuff is applied to the patient, used to make one or more blood pressure measurements, and then removed. Going forward, the calibration measurements are used, along with a change in PAT, to determine the patient's blood pressure and blood pressure variability. PAT typically relates inversely to blood pressure, i.e., a decrease in PAT indicates an increase in blood pressure.

The above described systems have a number of drawbacks including, for example, they require electrodes and sensors to be placed across multiple different locations of the patient; they require use of two different types of devices, namely, an ECG electrode set and reader, and a pulse oximetry device; they have an increased risk of waveform detection error arising from the need of the ECG; and they require a finger clip, which is inconvenient to wear for extended periods of time.

In view of the above, a more reliable, robust and convenient blood pressure monitoring device is desired.

SUMMARY OF THE INVENTION

A blood pressure monitoring device for computing mean arterial pressure of a user includes a case and a strap adapted to hold the case against the wrist of the patient. Sensors are arranged within the case and aimed at a capillary artery in the wrist when the case is strapped to the wrist. A processor is arranged within the case and operable to: compute a plurality of features from the data generated by the sensors; and compute the mean arterial pressure (MAP) based on the plurality of features.

In embodiments, a method for monitoring mean arterial pressure (MAP) of a person comprises: activating at least two PPG probes aimed at the capillary arteries in the wrist of the person to generate velocity data; and automatically computing on a processor: a plurality of features from the PPG velocity data; and the MAP of the user based on the plurality of features.

Optionally, SBP and DBP are computed based on the plurality of features.

In embodiments, a display on the case presents the blood pressure information to the user.

In embodiments, a blood pressure monitoring system for computing mean arterial pressure of a user comprises: a case and a window adapted to be held against the skin of the patient; at least two PPG probes arranged within the case; and a processor. The processor is arranged and operable to: compute a plurality of features from velocity data arising from two or more of the PPG probes; and to compute the mean arterial pressure (MAP) based on the plurality of features.

In embodiments, a light emitter directs light through the window towards the artery. In embodiments, a light emitter is incorporated into the PPG probe. In other embodiments, a light emitter, independent of the PPG probes, is arranged in the case and directs light through a window towards the artery. The PPG velocity data is based, at least in part, on the absorption of the light by the artery and blood flow therethrough.

In embodiments, the plurality of features comprises viscosity, heart rate, and blood oxygenation.

In embodiments, the plurality of features comprises: diastolic velocity, systolic velocity, systolic volume, diastolic volume, diastolic distance, systolic distance, heart rate, diastolic time, and/or systolic time.

In embodiments, the processor is further operable to compute diastolic blood pressure (DBP) based on the velocity data, and optionally, to compute systolic blood pressure based on the computed MAP and DBP.

In embodiments, the blood pressure monitoring system comprises a trained model for determining MAP based on the plurality of features extracted from the velocity data.

In embodiments, the blood pressure monitoring system further comprises a console, and the processor is enclosed within the console. The case, window, and at least two PPG probes can be incorporated together as a handheld tool connected to the console by an umbilical cord.

In embodiments, the blood pressure monitoring system is arranged in the form of a thin patch, and optionally, the system includes an adhesive layer to bond the patch to the skin.

In embodiments, a device, method or system is programmed and operable to compute MAP, wherein the computing MAP is based on peripheral PPG velocity data obtained from multiple PPG sensors arranged to read only one peripheral region of skin, and optionally, wherein the skin region is a segment of skin along the outside of the wrist.

In embodiments, the sensors are aimed at different locations within the same anatomical part of the body. Preferably the target locations are within 50 mm and, more preferably, within 35 mm from each other. Examples of distinct anatomical parts of the body at which all the sensors are aimed include a finger, wrist, upper arm, thigh, chest, neck, and ear.

In embodiments, the sensors do not simultaneously measure data from different anatomical parts of the body. For example, in embodiments, the sensors of the system are not simultaneously aimed at both the chest and the wrist. In embodiments, the sensors of the BP monitoring system are aimed at solely one anatomical body part or another, and detect volume flow data from the only one body part.

In embodiments, the processor is operable to prompt the user for an actual blood pressure-related reading (e.g., an oscillometric compressive cuff), and to compute a patient-specific proportionality factor (e.g., $P_f$) based on the actual blood pressure-related reading, and wherein the MAP is based on the patient-specific proportionality factor.

In embodiments, the data arising from the sensor modality is velocity data and volume flow data through the vessel of the patient, and the processor is programmed and operable to compute BP values of the patient based on the volumetric flow data (or features extracted or computed therefrom). In some embodiments, the BP values are computed based on the volumetric flow data of the patient and without using BP databases to correlate pressure with the sensor data.

Without intending to be bound to theory, computing BP values based on the patient volumetric flow data itself is more accurate than use of a database to match BP values to the PPG signal because of possible errors that may arise when generating the database. Possible errors can arise due to human, hardware and software differences between users and hospitals. In view of the time scale, a small difference in time may have a significant impact on the calculation of the BP values. Thus, in some embodiments of the present invention, databases of BP values (correlated with sensor signals) are avoided.

Advantages of Embodiments of the Present Invention

Embodiments of the present invention are capable of determining the pressure values without measurement of elevation, or elevation changes.

Embodiments of the present invention are capable of determining the pressure values without measurement of distention, or distension changes.

Embodiments of the present invention are capable of determining the pressure values without measurement of air pressure, or air pressure changes.

Embodiments of the present invention are capable of determining the pressure values without measuring information at multiple anatomical areas.

Embodiments of the present invention are capable of determining the pressure values without using ECG data.

Embodiments of the present invention are capable of continuously monitoring BP pressure values without compression.

Embodiments of the present invention are capable of determining the pressure values based on the photoplethysmography velocity data arising from a non-invasive wearable bracelet-like device.

Still other descriptions, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

U.S. Patent Pub. No. 20220225885, filed Dec. 28, 2021, entitled "Non-Invasive Non-Compressive Blood Pressure Monitoring Device" to Jeffrey Loh is incorporated herein by reference in its entirety for all purposes.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Overview

Figure 1:
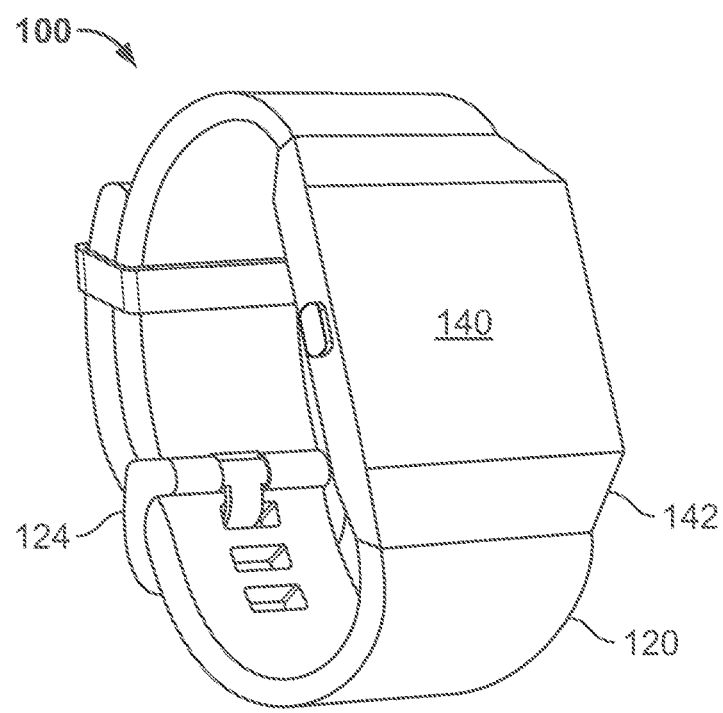
FIG. 1 is front side perspective view of a blood pressure monitoring device in accordance with one embodiment of the invention.

FIG. 1 illustrates a blood pressure monitoring device 100 in accordance with an embodiment of the invention. The blood pressure monitoring device 100 is shown having a strap 120, buckle 124, and a display 140 arranged on a case 142. The strap and case are sized and operable to be snugly fastened to the human wrist (not shown) and without compressing, occluding, distending, or otherwise interfering with the user's vasculature.

Figure 2:
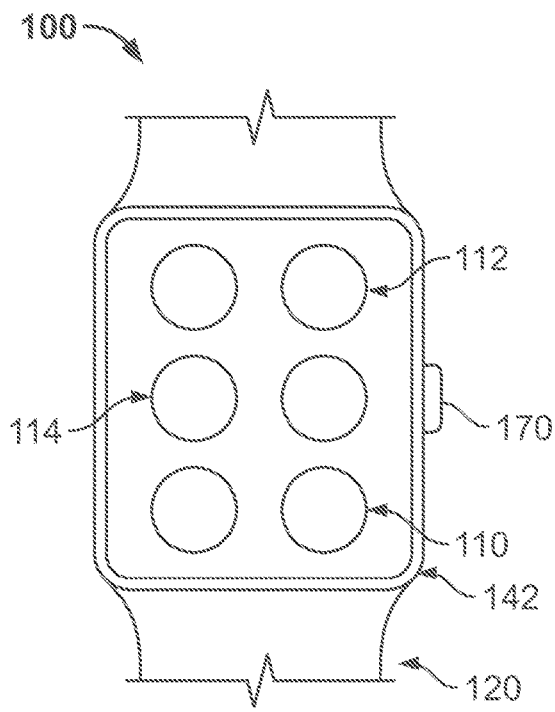
FIG. 2 is an enlarged rear view of a portion of the blood pressure monitoring device shown in FIG. 1.

With reference to FIG. 2, the backside of the case 142 shows a plurality of pairs of sensors or probes 110, 112, 114 for obtaining blood flow information from which blood pressure values are automatically computed, discussed further herein. In embodiments, a thin window or protective layer is disposed over the sensors on the backside of the case. The window can be made of material that permits acoustic and/or electromagnetic waves to pass therethrough.

Figure 3:
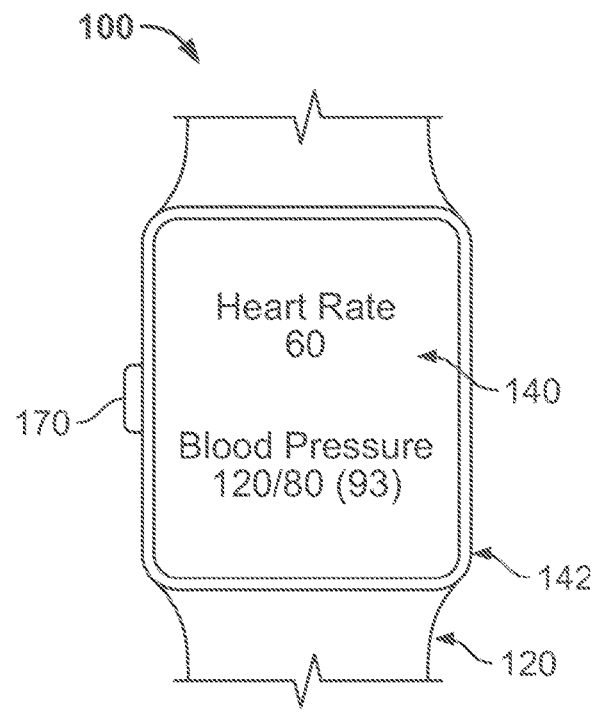
FIG. 3 is an enlarged front view of a portion of the blood pressure monitoring device shown in FIG. 1.

With reference to FIG. 3, the display 140 is operable to show various blood pressure information including, without limitation, heart rate (HR), systolic blood pressure (SBP), diastolic blood pressure (DBP), mean arterial pressure (MAP), and optionally date and time. Optionally, one or more buttons 170 are located on the case for controlling the device to carry out various functions such as for, example, calibration mode, location (or sensor-location adjustment) mode, and/or monitoring mode, discussed further herein.

Figure 4:
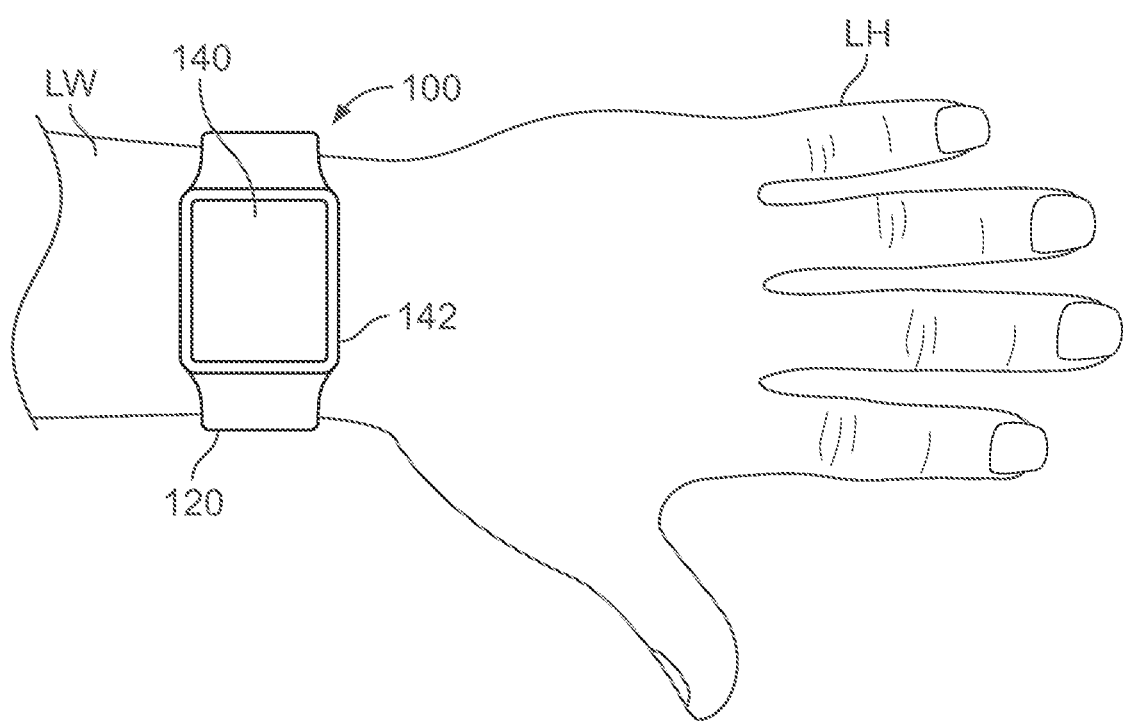
FIG. 4 shows a front view of a blood pressure monitoring device placed on the left wrist in accordance with an embodiment of the invention.

FIG. 4 shows a blood pressure monitoring device 100 fastened to the left wrist (LW) of a user in accordance with an embodiment of the invention. The rear side of the case lies flat against the outside of the left wrist when fastened.

In embodiments, the device comprises a location mode or module that is operable to select which sensor or sensor pair shall be used for the blood pressure monitoring mode. In embodiments, the device is programmed to automatically evaluate which sensor or sensor combination is best based on which sensor or sensor combination shows the greatest signal pickup. Optionally, (e.g., if signal perception is less than sufficient), the device will prompt the user to move/adjust the location of the device along the user's skin until an optimal signal is detected, discussed further herein. The location mode can thus provide an optimum sensor combination for each location, as well as an optimum location in view of each of the sensor combinations available for the device.

Additionally, in embodiments, during the blood pressure monitoring mode, the device is operable to automatically periodically check each of the sensors for signal strength, and to select the sensor combination with the greatest signal. This step serves to continuously ensure that the optimal sensors are used for blood pressure monitoring.

System Architecture

Figure 5:
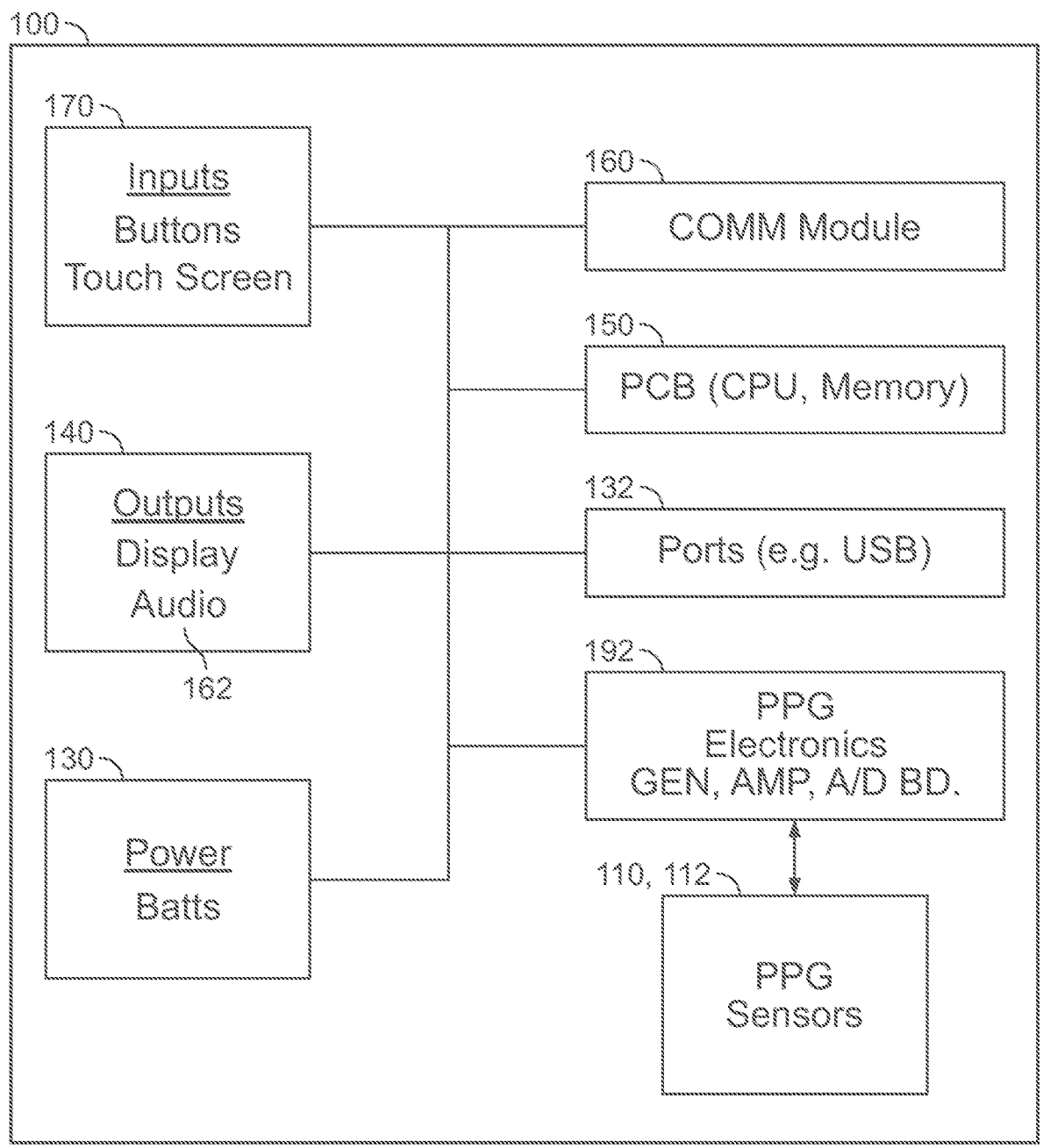
FIG. 5 is a block diagram of the blood pressure monitoring device in accordance with one embodiment of the invention.

FIG. 5 is a block diagram of a blood pressure monitoring device 100 in accordance with an embodiment of the invention. The device includes a plurality of PPG sensors 110, 112, PPG electronics 192, and a main printed circuit board 150 supporting a CPU and memory. As discussed further herein, the CPU, memory and electronics are operable to control the probes and to evaluate the PPG signals arising from the probes. Preferably, there are 2-10 PPG probes arranged in the case such that when the device is fastened to the wrist of the user several of the probes are in close proximity to the arteries to be interrogated. In embodiments, the case holds 2-6 PPG sensors arranged as shown in FIG. 2.

FIG. 5 also shows power (preferably a rechargeable battery) 130, outputs (e.g., a display 140 or speaker 162), communication interface 160 (preferably a wireless near field communication module such as Bluetooth), port(s) 132 for charging the battery and/or transmitting data to and from the device via a charging cable such as a USB charging cable, and inputs 170 (e.g., buttons or touchscreen) all of which are in communication with one another.

Preferably the port(s) 132 have a low-profile design adapted to connect to a standard charging cable interface (e.g., a 2-pin magnetic, clip-type, or USB-C-type connector).

The memory stores data, information, and computer programs containing instructions for the CPU or other components of the blood pressure monitoring device 100. The types of information stored may vary and include, without limitation, raw data of sensor signals, models and algorithms for processing the data, processed sensor signals, extracted features, patient personal information, vitals, SVP, DBP, HR, MAP. Examples of memory include volatile (e.g., RAM) and non-volatile memory types of memory. In embodiments, the system includes a flash memory device for storing and recording new data. Indeed, the invention is intended to include a wide range of types of memory, processor, and circuit frameworks unless specifically excluded by any appended claims.

The device 100 is operable to alert the user based on evaluating the information. If information is outside a predetermined range, the device alerts the user. Examples of alerts include an audible alarm via audio component 162, a visual graphic indicated on the display 140, a text or email sent to the user or hospital care, etc. Examples of types of information which would generate an alert if outside the predetermined range include, without limitation, battery or power source level, vital value, MAP, SBP, or DBP values, etc.

Optionally, in embodiments, the information is transmitted to portable computing devices such as smart phones, tablets, and laptop computers. Additionally, in embodiments, a server (local or remote) is programmed and operable to communicate with the portable computing devices. Data may be recorded, stored, evaluated, and compiled by the server for backup and safekeeping, and to further update or train the BP models. Updated firmware, software, algorithms, models and Apps may also be downloaded from the server to the remote devices, and then to the PPG BP monitoring systems described herein.

Use of Photoplethysmography (Ppg) to Determine Map

In embodiments of the invention, PPG information obtained from the PPG sensors is utilized to determine MAP.

Figure 6:
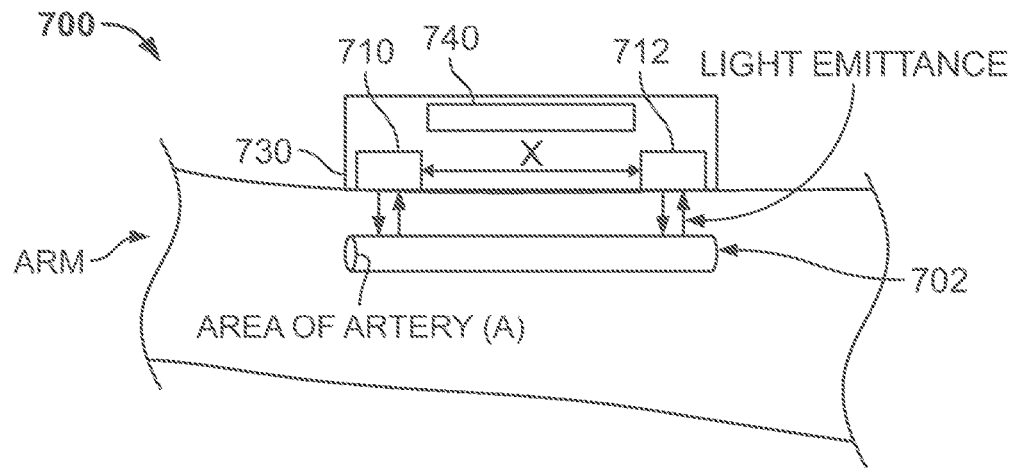
FIG. 6 is a schematic illustration of another blood pressure monitoring device in accordance with an embodiment of the invention.
Figures 7A, 7B:
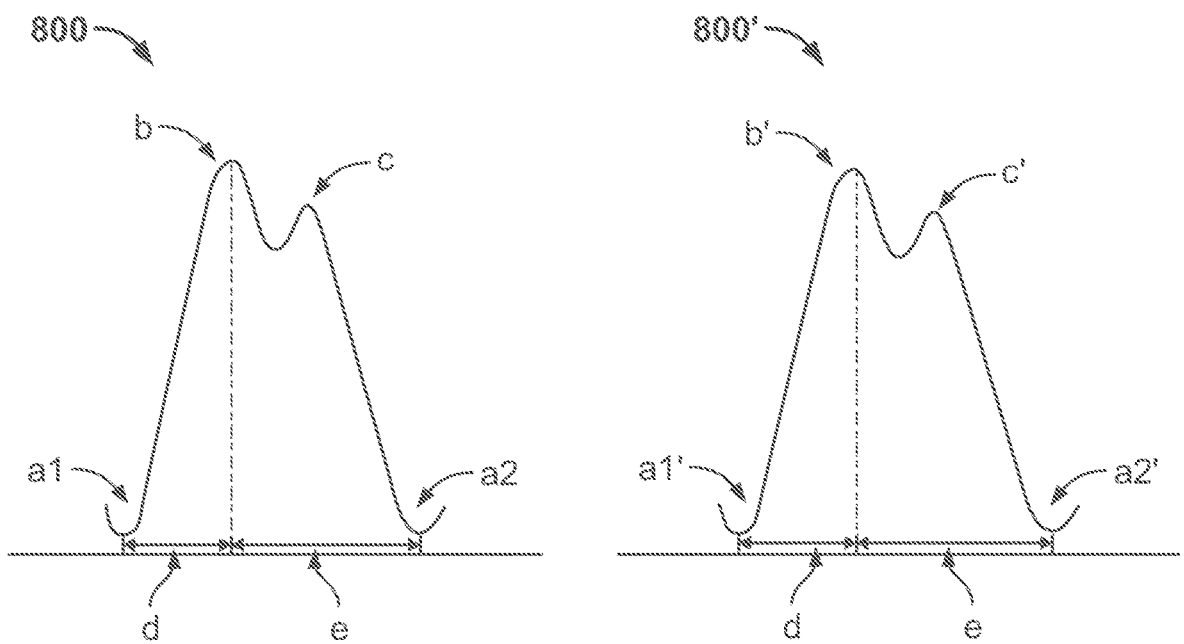
FIGS. 7A, 7B are exemplary PPG waveforms recorded by the blood pressure monitoring device shown in FIG. 12.

With reference to FIGS. 6-7B, a PPG system 700 and exemplary recorded PPG waveforms 800, 800' for deriving MAP are illustrated. PPG system 700 is shown having first PPG sensor 710 and second PPG sensor 712 arranged over the one or more capillary arteries of the patient or user's arm. The first PPG sensor 710 is spaced a fixed distance (X) from second PPG sensor 712. Each of the PPG sensors are operable to send and receive light several millimeters into the patient's arm. The PPG sensors can be embodied in a case 730 as described above in connection with FIG. 4. The PPG sensors can be arranged side by side with the other sensors (e.g., doppler, photoacoustic, other). In embodiments, the system includes a combination of different types of sensors. An exemplary PPG sensor is Valencell BW 4.0, manufactured by Valencell (Raleigh, NC).

In the embodiment shown in FIG. 6, system 700 includes PPG electronics 740. The PPG electronics 740 (optionally in the form of one or more PCBs) can include one or more processors, memory and storage devices, AD converters, communication modules (e.g., for hardwire or wireless), and power supply or interface connections.

In operation, the PPG sensors are operable with the PPG electronics to generate and record PPG waves as shown in FIGS. 7A, 7B as the blood travels through the vessel (e.g., the RA or other capillary arteries). As described further herein, the device is operable to extract and compute a number of the features from the blood pulse waves as they pass each of the PPG sensors 710, 712.

Ppg Sensor Method Overview

Figure 8:
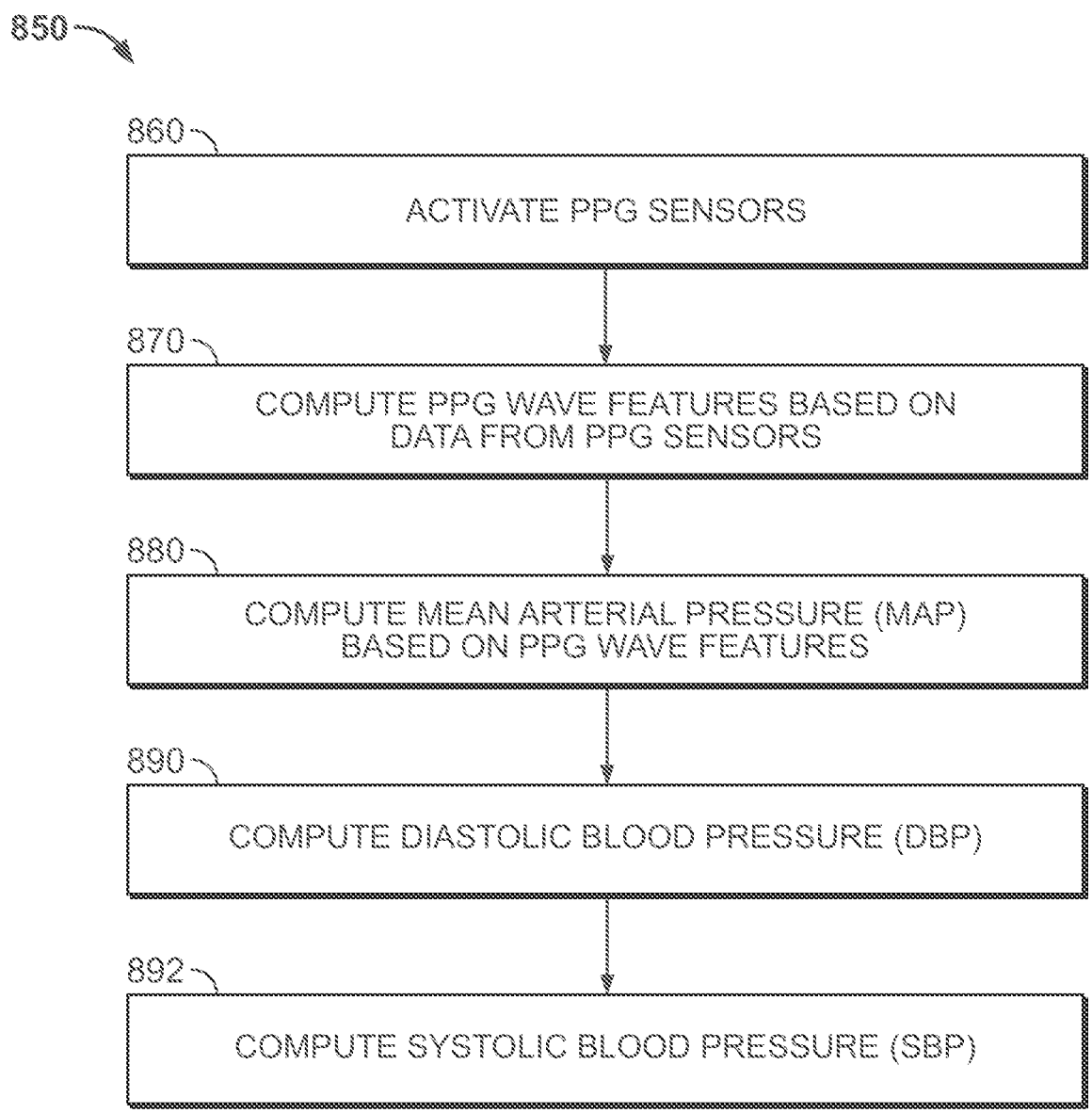
FIG. 8 is a flowchart illustrating an overview of a method for computing blood pressures based on PPG information in accordance with an embodiment of the invention.

With reference to FIG. 8, an overview of a method 850 for computing blood pressures in accordance with an embodiment of the invention is shown.

Step 860 states to activate the PPG sensors. This step can be performed by the user activating (namely, turning on) the PPG sensors 710, 712 shown in FIG. 6. When the sensors are embodied in a case 100 as shown in FIG. 1, the user may activate the sensors by toggling the button 170.

In embodiments, the system is programmed to continuously or periodically activate the sensors. In embodiments, a BP App stored on the user's portable computing device is operable to activate the sensors, and/or to create a BP monitoring schedule that controls when the sensors are activated. Unlike compressive-type BP monitors, embodiments of the present invention can activate and monitor BP in continuously in real time (e.g., every 60 seconds or less, or more preferable every 30 second or less).

Step 870 states to compute PPG wave features based on data generated by the PPG sensors. This step can be performed by sending the data generated by the PPG sensors and PPG electronics to a processor operable to extract and compute various features from the PPG waveform (e.g., waveform 800 and 800' shown in FIGS. 7A and 7B respectively). Waveform 800 is an example of data arising from the first PPG sensor 710 aimed at a capillary artery 702. The second PPG sensor, fixedly spaced from the first sensor within the case 100, is operable to generate a second waveform (800'). The processor is operable to extract and compute various features from the first and second waveforms 800, 800', and to compute features characterizing changes between the two waveforms. Examples of extracted features include, without limitation, pulse wave begin, systolic peak, diastolic peak, pulse wave end, and the time that each feature occurs. In embodiments, given the PPG waveform inputs, the processor is operable to automatically detect these features based on, e.g., assuming the highest and second highest amplitudes are the systolic and diastolic peaks, respectively, and the pulse end/begin is where the amplitude is minimum. Still in other embodiments, a trained model is applied by the processor to extract these features based on an input waveform.

As stated above, a number of features are automatically computed based on the extracted or detected features. Examples of computed features include, without limitation, heart rate, systolic and diastolic times, systolic and diastolic velocities, systolic and diastolic volumes, and systolic and diastolic distance travelled, as described further below in connection with FIG. 9.

Step 880 states to compute mean arterial pressure (MAP) based on the computed wave features. This step can be performed by the processor in accordance with computer readable instructions stored in the memory, as described in detail below with reference to FIG. 9.

Step 890 states to compute diastolic blood pressure (DBP). This step can also be performed by the processor in accordance with computer readable instructions stored in the memory, as described in detail below with reference to FIG. 9.

Step 892 states to compute systolic blood pressure (SBP). This step can also be performed by the processor in accordance with computer readable instructions stored in the memory, as described in detail below with reference to FIG. 9.

Figure 9:
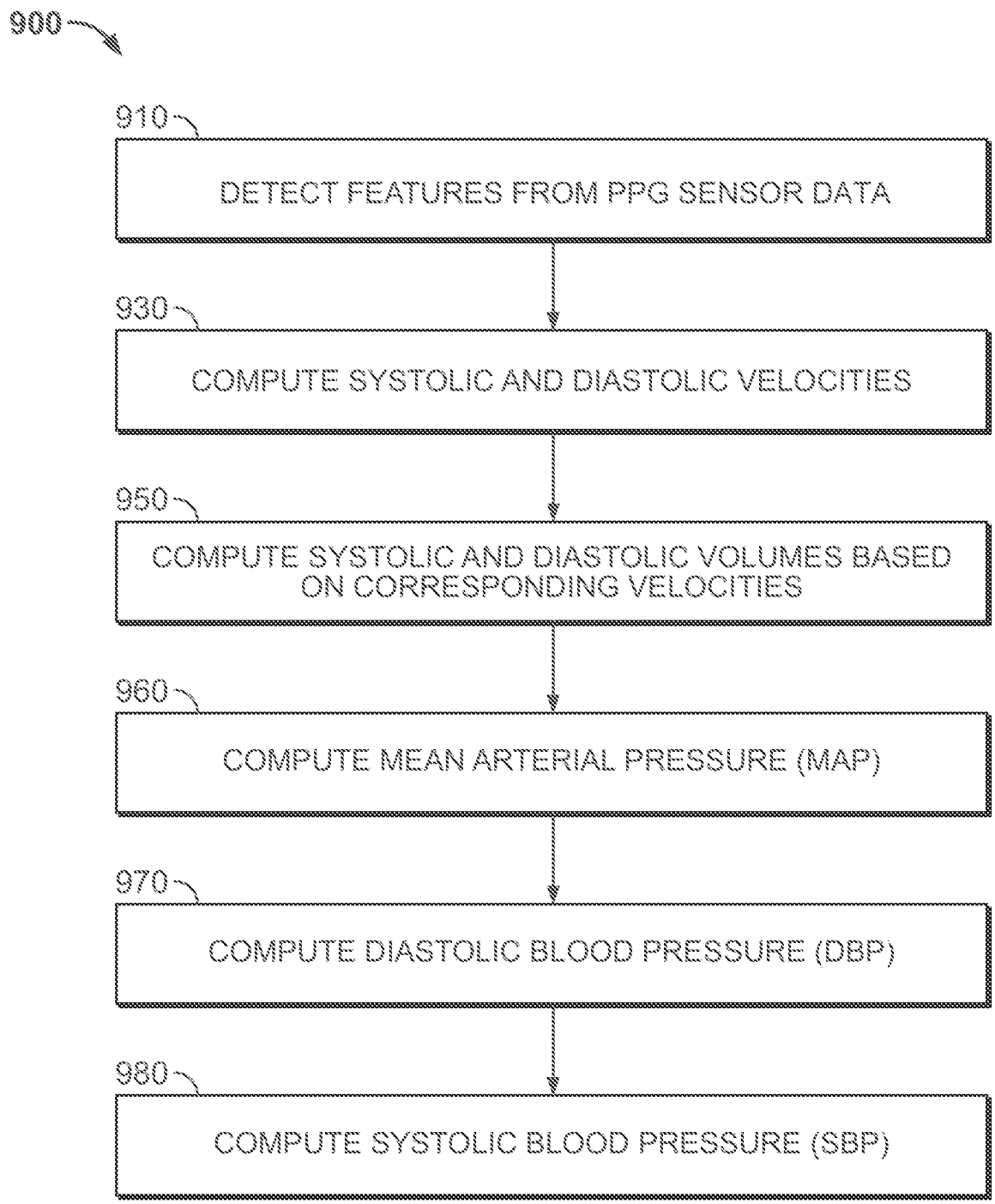
FIG. 9 is a flowchart illustrating another method for computing blood pressures based on PPG information in accordance with an embodiment of the invention.

With reference to FIG. 9, a detailed method 900 of computing blood pressure is shown based on PPG information arising from PPG sensors (e.g., PPG sensors 710, 712 shown in FIG. 6) in accordance with an embodiment of the invention.

Step 910 states to detect features from the PPG sensor data. In embodiments, the first PPG sensor 710 records the PPG waveform 800. The PPG waveform 800 shows various wave features including: pulse wave begin (a1), pulse wave systolic peak (b), pulse wave diastolic peak (c), and pulse wave end/begin (a2). The processor is operable to automatically detect the various features and to record the value and time for each feature, as described above.

Similarly, second PPG sensor 712, which is fixedly spaced a distance (X) from the first PPG sensor 710 as shown in FIG. 6, records the corresponding PPG waveform (800'). The device identifies the corresponding features from the second wave including: pulse wave begin (a1'), pulse wave systolic peak (b'), pulse wave diastolic peak (c'), and pulse wave end/begin (a2'). The processor is operable to automatically detect the various features and to record the value and time for each feature, as described above.

Step 930 states to compute systolic and diastolic velocities. This step is performed by the processor where that velocity is equal to distance divided by time.

The distance between the sensors is fixed and equal to x with reference to FIG. 6. In embodiments, X ranges from 1-20 mm, more preferably 15-35 mm, and optionally 25-50 mm.

Additionally, the time for the pulse wave systolic peak to travel between the sensors can be computed from the recorded PPG waveforms and is equal to (b'-b). In embodiments, the time (b'-b) ranges from about 5-40 ms, more preferably 10-20 ms. Thus, $$\text{Systolic velocity} = \frac{x}{b' - b}$$

Similarly, we calculate the diastolic velocity where the time for the pulse wave diastolic peak to travel between the sensors is (c'-c). Thus, $$\text{Diastolic velocity} = \frac{x}{c' - c}$$

Step 950 states to compute systolic and diastolic volumes based on corresponding velocities.

The systolic volume equals the systolic distance traveled multiplied by the area of the artery (A), where the systolic distance of the blood travel is equal to systolic velocity multiplied by time, and the area (A) may be determined by ultrasound or other means. We know the velocity and time as discussed above. Thus, $$\text{Systolic Distance of blood travel} = \frac{x}{b' - b} \times (b - a1)$$

And the systolic volume equals the systolic distance traveled multiplied by the area of the artery (A), or $$\text{Systolic Volume} = A \times \frac{x}{b' - b} \times (b - a1)$$

Similarly, the diastolic volume equals the diastolic distance traveled multiplied by the area of the artery (A), where the diastolic distance of the blood travel is equal to velocity multiplied by time. We know the velocity and time as discussed above.

Thus, the diastolic distance travelled is:

$$\text{Diastolic distance} = n \frac{x}{c' - c} \times (a2 - b)$$

And the diastolic volume equals the diastolic distance traveled multiplied by the area of the artery (A), or $$\text{Diastolic volume} = A \times \frac{x}{c' - c} \times (a2 - b)$$

Step 960 states to calculate the mean arterial pressure (MAP). This step is performed automatically on the programmed processor where MAP is equal to cardiac output (CO) multiplied by systemic vascular resistance (SVR), and where CO is equal to heart rate (HR) multiplied by stroke volume (SV), and stroke volume (SV) is equal to the systolic volume (computed in this embodiment according to step 950 above) multiplied by a proportional factor $P_f$, or Stroke Volume=Systolic Volume*$P_f$ $$= A \times \frac{x}{b' - b} \times (b - a1) \times Pf$$

where the proportionality constant $P_f$ can be computed as described herein. Thus, cardiac output (CO) can be determined according to the following:

$$CO = HR \times A \times \frac{x}{b' - b} \times (b - a1) \times Pf$$

where HR can be estimated based on the time for one pulse wave or (a2-a1) or 60/(a2-a1) beats per minute.

We also know that systemic vascular resistance (SVR) is equal to the change in pressure (Δp) divided by the volumetric flow (Δol$_f$). The pressure change (Δp) is approximately equal to change in velocity (or Δv) between the systolic velocity and the diastolic velocity, described above. Thus, the pressure change (Δp) is approximately equal to the following:

$$\text{pressure change}(\Delta p) = \left(\frac{x}{b'-b} - \frac{x}{c'-c}\right)$$

The volumetric flow ($\Delta ol_f$) can be approximated as the area of artery (A) multiplied by the mean systolic velocity, where the mean systolic velocity is equal to the (systolic velocity+diastolic velocity)/2, or $$\text{Mean Systolic Velocity} = \frac{1}{2} \times \left(\frac{x}{b'-b} + \frac{x}{c'-c}\right)$$

And, $$\text{Volumetric Flow}(Vol_f) = \frac{1}{2} \times A \times \left(\frac{x}{b'-b} + \frac{x}{c'-c}\right)$$

The systemic vascular resistance (SVR) can now be simplified as follows:

$$SVR = \text{Change in pressure}/Vol_f$$

$$= \frac{\left(\frac{x}{b'-b} - \frac{x}{c'-c}\right)}{\frac{1}{2} \times A \times \left(\frac{x}{b'-b} + \frac{x}{c'-c}\right)} = \frac{2 * \left(\frac{x}{b'-b} - \frac{x}{c'-c}\right)}{A \times \left(\frac{x}{b'-b} + \frac{x}{c'-c}\right)}$$

Inserting the CO and SVR into the equation for MAP provides:

$$MAP = CO \times SVR$$

$$= \frac{\left\{HR \times A \times \left[\frac{x}{b'-b}\right] \times (b-a1) \times Pf \times \left[2 \times \left(\left[\frac{x}{b'-b}\right] - \left[\frac{x}{c'-c}\right]\right)\right]\right\}}{A \times \left(\left[\frac{x}{b'-b}\right] + \left[\frac{x}{c'-c}\right]\right)}$$

$$= \frac{\left\{HR \times x \times (b-a1) \times Pf \times 2 \times \left(\left[\frac{x}{b'-b}\right] - \left[\frac{x}{c'-c}\right]\right)\right\}}{(b'-b) \times \left(\left[\frac{x}{b'-b}\right] + \left[\frac{x}{c'-c}\right]\right)}$$

where HR, a1, b, b', c, c' are automatically detected from the PPG waveforms and x is equal to the fixed distance between the sensors, as described above.

$P_f$ is initially calculated by calibrating the blood pressure device to a measured blood pressure reading using a clinically acceptable BP measuring device (e.g., a conventional oscillometric compressive cuff device as described above). By inputting an individual's current MAP blood pressure reading from a compressive blood pressure device, $P_f$ can be derived using the MAP algorithm listed above.

Step 970 states to calculate diastolic blood pressure (DBP). This step is performed automatically on the programmed processor.

Diastolic blood pressure(DBP)=diastolic output (DO)× SVR, where DO is equal to HR×diastolic stroke volume.

As described above, HR can be measured directly by the PPG sensors and SVR can be computed as described above. The diastolic volume can be computed from the following equation:

Diastolic Stroke Volume(*DSV*)=Diastolic Volume*Proportional Factor (*Pd*), or $$DSV = A \times \left(\frac{x}{c'-c}\right) \times (a2-b) \times Pd$$

Inserting the HR, SVR and diastolic stroke volume into the equation for diastolic blood pressure (DBP) provides:

$$DBP = \frac{HR \times A \times \left(\frac{x}{c'-c}\right) \times (a2-b) \times Pd \times \left[2 \times \left(\frac{x}{b'-b} - \frac{x}{c'-c}\right)\right]}{A \times \left(\frac{x}{b'-b} + \frac{x}{c'-c}\right)}$$

$$= \frac{HR \times x \times (a2-b) \times Pd \times 2 \times \left(\frac{x}{b'-b} - \frac{x}{c'-c}\right)}{(c'-c) \times \left(\frac{x}{b'-b} + \frac{x}{c'-c}\right)}$$

Pd is a diastolic proportionality factor and can initially be calculated by calibrating the blood pressure device to a measured blood pressure reading using a clinically acceptable BP measuring device (e.g., a conventional oscillometric compressive cuff device as described above). By inputting an individual's current diastolic blood pressure reading from a compressive blood pressure device, Pd can be derived using the DBP algorithm listed above.

Step 980 states to calculate systolic blood pressure (SBP). This step is performed automatically on the programmed processor.

SBP may be approximated according to the following equation:

MAP=DBP+(SBP−DBP)/3.

This implies that SBP=(3×MAP)−(2×DBP), where MAP and DBP can be computed as described above.

Computational Model

Although exemplary models were described above for automatically computing blood pressure values (including, for example, MAP, SBP, DBP) based on the sensor data, a wide variety of models may be used to compute the blood pressure from the features extracted from the recorded waveforms. In embodiments, a machine learning or AI model is trained and employed to estimate the blood pressure values based on one or more of the features described above. Examples of suitable models include without limitation artificial neural networks (e.g., trained CNN). In embodiments, a CNN is trained on user data to correlate the various extracted features (such as the extracted features described above) to the blood pressures.

Function approximation using machine learning (e.g., deep neural nets) is described in various publications such as, for example, Jonas Adler et al, "Solving ill-posed inverse problems using iterative deep neural networks", Inverse Problems, Volume 33, Issue 12, (2017). The function approximation model can be trained on data gathered through simultaneously value recording using the novel PPG blood pressure monitoring device described herein and a sphygmomanometer on a diverse group of subjects. The above described extracted features are correlated with the actual measured BP values. Ultimately, it is anticipated the trained model would not require calibration (e.g., to determine $P_f$ or $P_d$) for each user.

Figure 10:
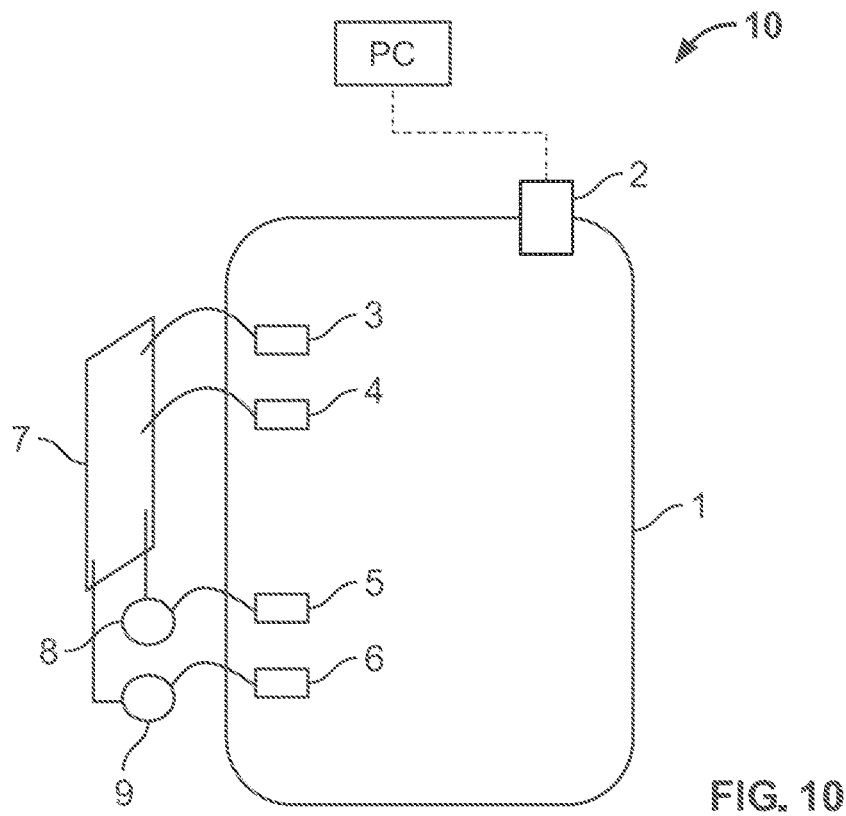
FIG. 10 is a block diagram of a PPG system including a microcontroller and sensors in accordance with an embodiment of the invention.

FIG. 10 Prototype Implementation

FIG. 10 shows one implementation of a PPG signal acquisition system 10 in accordance with an embodiment of the invention. The system 10 is shown including a microprocessor board 1 (e.g., the UNO R3 board manufactured by Arduino S.r.l.) which functions as a microprocessor to collect and transmit PPG signals from PPG sensor assembly 7.

PPG sensor assembly 7 is shown including a board, and PPG sensor 8 and PPG sensor 9. In embodiments, each PPG sensor 8, 9 of the assembly has the following characteristics:
 a) diameter=0.625" (~16 mm);
 b) overall thickness=0.125" (~3 mm);
 c) cable length=24" (~609 mm) (or less, or may be cut to desired length);
 d) voltage=3 V to 5 V;
 e) current consumption=~4 mA at 5 V;
 f) ambient light sensor (e.g., APDS-9008 from Avago); and
 g) a green light source (e.g., AM2520ZGC09 from Kingbright).

However, it is to be understood that a wide range of PPG sensor assemblies may be utilized to carry out the invention except as where limited by any appended claims.

Power can be supplied to microprocessor board 1 through jack 2 (e.g., USB port). The sensor board 7 is shown receiving its power through connections 3, 4 (e.g., a 5 V pin and ground pin). Optionally, a rechargeable battery (not shown) is arranged in connection with the microprocessor board 1 and the jack 2 can be used to charge the battery.

The PPG sensors 8, 9 are also shown connected to the microprocessor board at pins 5 and 6, respectively. The PPG signal is sent to the board through these pins and converted by an Analog to Digital converter (ADC) on the microprocessor. In embodiments, the ADC is capable of representing analog voltages by 1,024 digital levels. The ADC converts voltage readings into bits of information which the microprocessor can understand. The digitized information is transmitted to an onboard processor and memory, and optionally to a portable computing device or personal computer (namely, PC) via the jack or port 2.

The implementation shown in FIG. 10 provides a convenient approach to obtain PPG data from two locations of the wrist. PPG signals from the sensors 8, 9 are transmitted to the processor and stored (e.g., as a csv file). This data is then input to the algorithm module or hub, described herein for computing MAP and other vitals.

Figure 11:
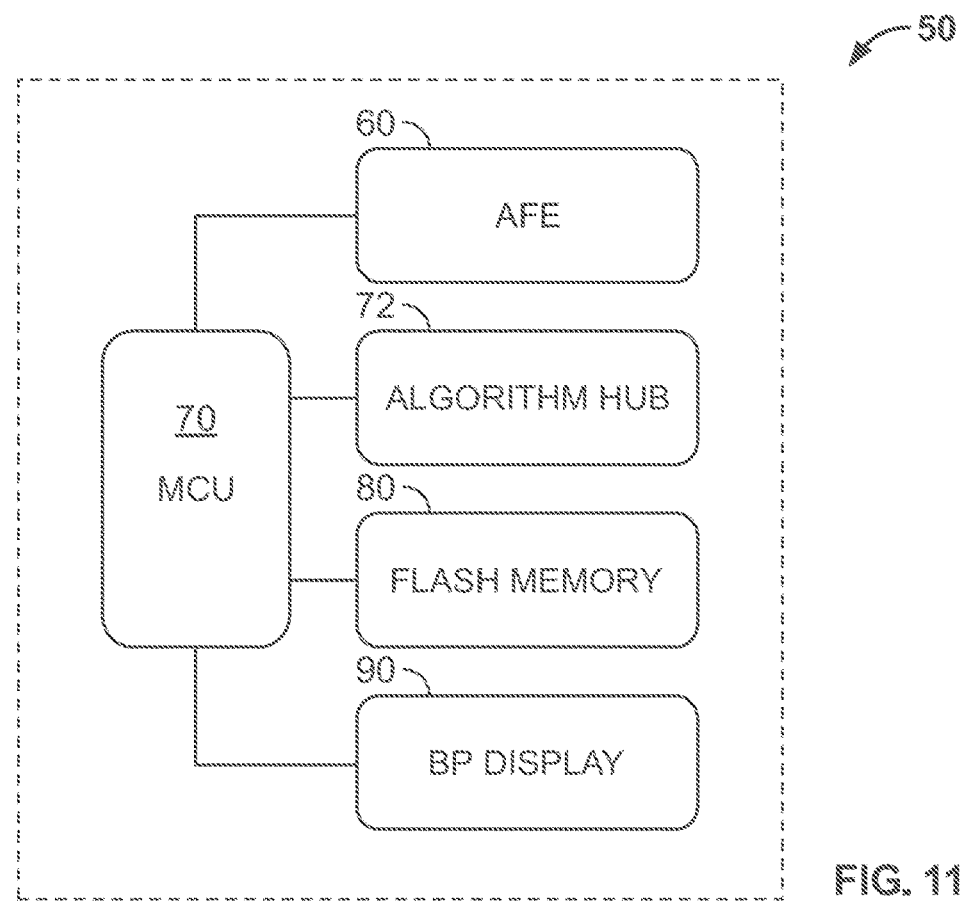
FIG. 11 is a block diagram of another PPG data acquisition system including microcomputer and electronics in accordance with an embodiment of the invention.

FIG. 11 Miniaturized Implementation PPG Acquisition System

FIG. 11 is an embodiment of a miniaturized PPG signal acquisition system 50 including an integrated chip sensor 60, microcontroller unit 70, algorithm hub 72, memory 80, and display 90.

The integrated chip sensor is operable with the PPG sensors described herein to receive analog signals from each PPG sensor. Examples of suitable integrated chip sensors include, without limitation, analog front end chip-type integrated sensors.

A preferred integrated chip for PPG data acquisition is the MAX86176 ECG & PPG Analog Front End manufactured by Maxim Integrated (San Jose, California). It has the following characteristics: a) 2.728 mm×2.708 mm Wafer Level Packaging Package; b) supports Frame Rates from 1 fps to 2 kfps; c) supports up to 6 LEDs and 4 photodiode inputs; d) High-Resolution 20-bit Charge-Integrating ADCs; and e) CMRR>110 dB at Power-Line Frequencies. However, other small sensor acquisition systems or AFE-type chips may be used having capabilities operable for powering, receiving, filtering and converting the PPG signals to digital data for processing.

FIG. 11 also shows a microcontroller unit 70 which is operable with a customized algorithm hub 72 to evaluate the PPG data collected from the sensors and to extract and compute features, and to ultimately calculate the desired BP and vital values.

The microcontroller 70 is also shown being in communication with memory 80 (e.g., flash memory) for reading, writing, and storing data and results.

FIG. 11 also shows a display 90, on which the various information (e.g., BP values) can be displayed.

Optionally, a wireless communications module may be included in the system 50 to transmit information wirelessly to another device. The system 50 may be equipped with, e.g., blue tooth technology to send information to a portable computing device such as a smartphone, tablet or computer.

The portable computing device may be programmed using an App to operate with the PPG acquisition unit 50 to sync data and values, user information, and display user history and data.

Optionally, the system may include a remote or cloud server programmed and operable to communicate with the portable computing devices through the internet and to record all user data and to download new versions of the App and BP algorithms onto the portable computing devices. In embodiments, the BP algorithm can be updated on the server (e.g., adjusting the proportionality factors or the machine learning algorithm described above) based on collecting more user BP data as well as user inputs such as age, weight, height, calibration cuff pressure, etc. The BP algorithm can then be downloaded to the updated portable computing device, and then ultimately downloaded to the wearable BP measuring device.

Figure 12:
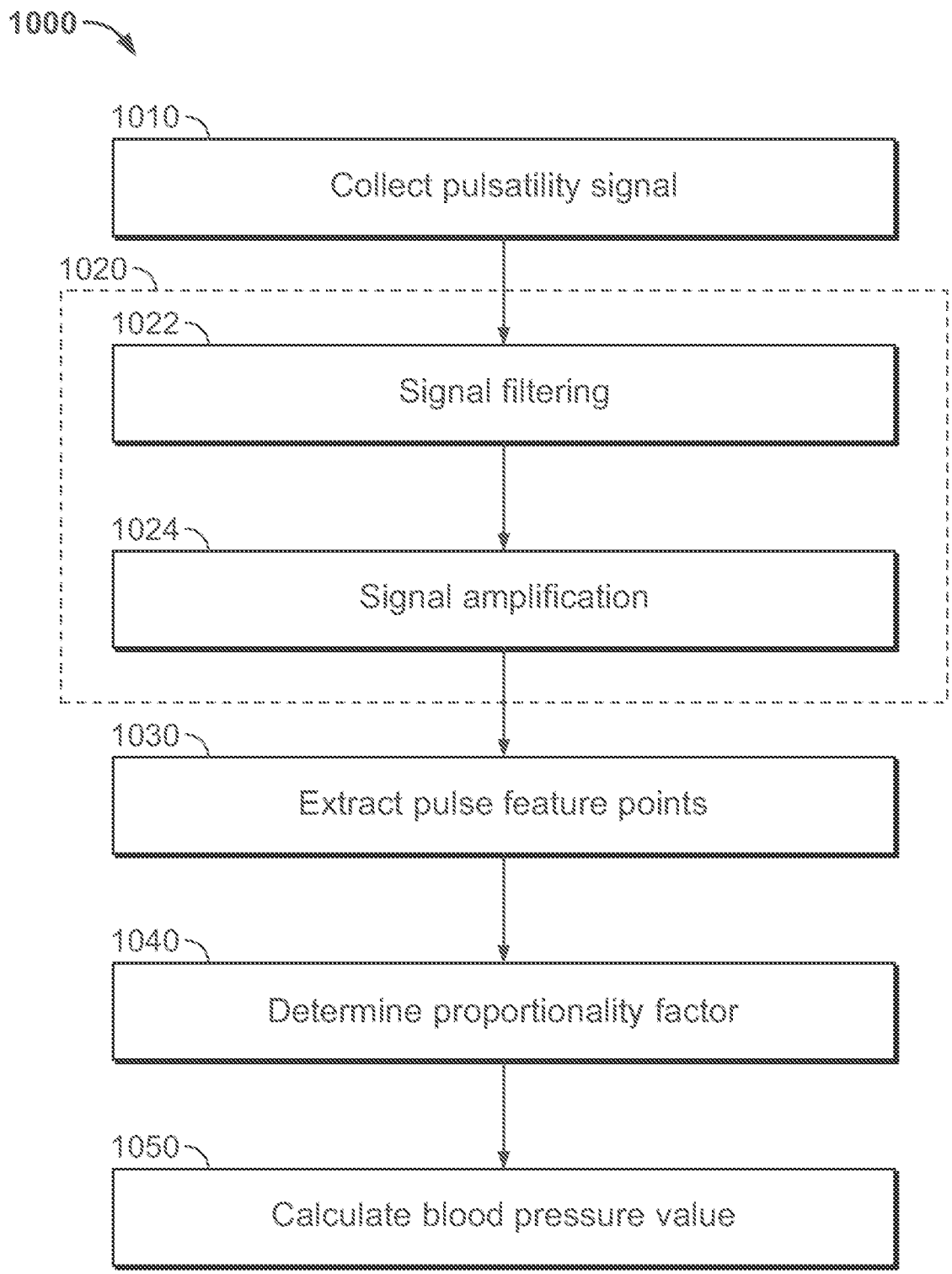
FIG. 12 is a flowchart illustrating another method for computing blood pressures based on PPG information in accordance with an embodiment of the invention.

FIG. 12 is a flow chart illustrating another method 1000 for calculating blood pressure based on PPG data.

Step 1010 states collect pulsatility data. This step may be performed by activating PPG sensors (e.g., PPG sensors 8, 9 described above) arranged in a watch or another type of wearable apparatus to obtain analog data of the blood flow.

Step 1020 is signal processing. In embodiments, signal processing or pre processing is performed by the sensor board or an AFE chip to filter 1022, and amplify 1024, and convert to digital, the PPG signals.

Step 1030 states to extract pulse feature points. In embodiments, this step is performed by evaluating the signals from step 1020 for feature points as described above in connection with FIGS. 7A, 7B such as, for example, a, a', b, b', c, c', a2, a2', c, and d. This step may be performed by an algorithm to identify the cycles, and valleys (minima) and peaks (maxima) in each cycle. This step may be performed by a microprocessor in combination with an algorithm hub in the PPG acquisition system 50, 100 described above in connection with FIGS. 5, 11.

Step 1040 states to determine the proportionality factor. In embodiments, this step is performed by calibrating the blood pressure device to a measured blood pressure reading using a conventional BP measuring device such as a conventional oscillometric compressive cuff device. By inputting an individual's current blood pressure (MAP or DBP) reading from a compressive blood pressure device, the proportionality factor ($P_f$ or Pd, respectively) can be derived using the equations for MAP and DBP listed above. After the proportionality factors are initially determined, this step may be omitted during continuous monitoring.

Step 1050 states to calculate blood pressure value. In embodiments, this step is performed by computing MAP from the equations described herein and based on the feature points and proportionality factor determined in the above steps 1030, 1040. This step may be performed by a microprocessor in combination with the algorithm hub in the PPG acquisition system 50, 100 described above in connection with FIGS. 5, 11. The algorithm hub or another storage can hold the various algorithms for determining the different blood pressure values and other vitals.

Next, the other blood pressure values (e.g., DBP and SBP) are computed as described above.

ALTERNATIVE EMBODIMENTS

Although the apparatus is described as arranged on the wrist, it could be configured otherwise. The device could be configured to read blood velocity data from another part of the body where there is an artery that is close to the surface of the skin. Examples of other configurations include, without limitation, handheld probes (with or without umbilical cord for electronic cabling), patches (optionally with adhesive), clips (e.g., for the ear), rings, and belts whether surrounding the chest, waist, thigh or another area.

Additionally, it is to be understood that data, program updates, and other communications can be transmitted between the BP monitoring device, portable computing device, and a local area network or a remote server or cloud.

It is also to be understood that, in embodiments, the BP monitoring device may be operable to be controlled by a remote device such as a tablet, smart phone or laptop.

Additionally, in other embodiments, additional types of sensors are combined or substituted for one or more of the sensors. For example, with reference to FIG. 2, one or more of the individual PPG probes of pairs 110, 112 may be replaced with doppler or a light emitter and detector. Preferably, the sensors are self-contained/stand-alone and include their own processing electronics to provide a signal to the CPU. However, in embodiments, less sophisticated emitters and detectors and cameras may be incorporated into the apparatus and the raw data sent to the processor for pre-processing and evaluation. In embodiments, doppler probes are combined with PPG sensors. Ultrasound energy from the doppler probe is used to create a temporary distortion in one PPG waveform. The multiple PPG sensors are then better able to determine the number of pulse waves that transit between the 1st and 2nd PPG sensor for the distance (X) they are spaced apart, by looking at when each PPG sensor detects an ultrasound-distorted waveform.

In embodiments the apparatus includes a plurality of modes of operation including without limitation a location mode, calibration mode, and/or monitoring mode.

In embodiments, the vessel location mode or module is operable to alert the user to an optimal position on the skin to hold the apparatus. This location mode (versus the above described blood pressure monitoring modes) may be activated by the user to commence energy delivery into the skin. In the location mode the energy emitters transmit energy into the skin and the electronics send the processed data to the main processor for evaluation. In embodiments, the processor is operable during the location mode to alert the user (e.g., via sound, vibration, or visual indicator) to the optimal position as the user moves the apparatus (whether a wearable or handheld device) along the skin. The user can scroll back and forth along a skin area to search for an optimal position. The audio indicator may be operable to increase in volume or pitch as the measured blood velocity increases.

Similarly, the device can be operable to provide visual feedback (e.g., light color or brightness) or tactile feedback (e.g., vibration generated by a small electromechanical actuator or motor) corresponding to a change in velocity with position along the skin. Once the user is satisfied with the position, the user straps or holds the device in place and activates the blood pressure monitoring mode.

In embodiments, the calibration mode prompts the user for a blood pressure reading (or another blood pressure-related parameter such as stroke volume) taken by alternative means (e.g., an oscillometric compressive cuff device, catheter, etc.). The proportionality factor of the user is automatically computed by the apparatus by equating a reading as measured by the apparatus itself (e.g., apparatus 100 and assuming a placeholder/estimate value for $P_f$), and the actual reading as measured by the alternative device (e.g., an oscillometric compressive cuff) and solving the equations described herein for the proportionality factor $P_f$. In preferred embodiments, the calibration mode prompts the user to repeat calibration several times until the proportionality factor is constant.

In embodiments, the monitoring mode can be performed subsequent to the location and calibration mode.

Although a number of embodiments have been disclosed above, it is to be understood that other modifications and variations can be made to the disclosed embodiments without departing from the subject invention. Indeed, any of the components described herein may be combined with one another except where such components are exclusive to one another. Any of the steps described herein may be combined in any combination and sequence except where such steps are exclusive to one another.

The invention claimed is:

1. A blood pressure monitoring device for computing mean arterial pressure of a user comprising:
   a case and a strap adapted to hold the case against the wrist of the patient;
   a first PPG sensor, including a light source and light sensor, within the case and aimed at a first location along an artery in the wrist when the case is strapped to the wrist;
   a second PPG sensor, including a light source and detector, spaced a fixed distance from the first PPG sensor within the case and aimed at a second location along the artery in the wrist when the case is strapped to the wrist; and
   a processor arranged within the case and operable to:
      compute a plurality of features from PPG waveform data generated by the first and second PPG sensors, wherein the plurality of features comprise computing diastolic velocity and systolic velocity based on the fixed distance; and
      compute the mean arterial pressure (MAP) based on the plurality of features.

2. The blood pressure monitoring device of claim 1, wherein computing MAP is further based on a predetermined proportionality coefficient associated with the user, wherein the proportionality coefficient is initially computed and based on measuring blood pressure using a second type of blood pressure measurement device.

3. The blood pressure monitoring device of claim 1, wherein one of the plurality of features comprises: systolic volume, diastolic volume, diastolic distance, systolic distance, heart rate, diastolic time, and/or systolic time.

4. The blood pressure monitoring device of claim 1, wherein the processor is further operable to compute diastolic blood pressure (DBP).

5. The blood pressure monitoring device of claim 1, wherein the processor is further operable to compute systolic blood pressure based on the computed MAP and DBP.

6. The blood pressure monitoring device of claim 1, wherein the case further houses a battery, memory, and PPG electronics.

7. The blood pressure monitoring device of claim 1, further comprising a trained machine learning model for determining the MAP based on the plurality of features extracted from the PPG waveform data.

8. The blood pressure monitoring device of claim 1, further comprising a display, and wherein the strap, case and display collectively form a wrist watch-like shape.

9. The blood pressure monitoring device of claim 1, further comprising a location module for alerting the user to an optimal position on the wrist to strap the case thereto as the user adjusts the position of the case along the user's wrist.

10. The blood pressure monitoring device of claim 1, wherein the MAP computing is performed without use of ECG data.

11. A blood pressure monitoring system for computing mean arterial pressure of a user comprising:
   a case and a window adapted to be held against the skin of the patient;
   at least one sensor modality arranged within the case wherein the at least one sensor modality comprises a first PPG sensor and second PPG sensor spaced a fixed distance from the first PPG sensor and aimed through the window towards the artery; and
   a processor arranged and operable to:
      compute a plurality of features including velocity information based on the fixed distance and data arising from the first PPG sensor and the second PPG sensor; and
      compute the mean arterial pressure (MAP) based on the plurality of features including the velocity information.

12. The blood pressure monitoring system of claim 11, wherein computing the MAP is performed without use of ECG data.

13. The blood pressure monitoring system of claim 11, wherein one of the plurality of features comprises: diastolic velocity, systolic velocity, systolic volume, diastolic volume, diastolic distance, systolic distance, heart rate, diastolic time, and/or systolic time.

14. The blood pressure monitoring system of claim 11, wherein computing MAP is further based on a predetermined proportionality coefficient associated with the user, wherein the proportionality coefficient is initially computed and based on measuring blood pressure using a second type of blood pressure measurement device.

15. The blood pressure monitoring system of claim 11, further comprising an adhesive to bond the case to the skin.

16. The blood pressure monitoring system of claim 11, further comprising an umbilical cord extending from the case for transmitting information to and from the case to another device, and optionally, to transmit power to the case from another device.

17. The blood pressure monitoring system of claim 11, wherein the features are computed from the velocity information flow data.

18. The blood pressure monitoring system of claim 17, wherein the MAP is computed without the use of database, atlas or general population-type information.

19. The blood pressure monitoring system of claim 11, wherein all the sensors are aimed at the same anatomical body part, and spaced less than 50 mm from one another.

20. The blood pressure monitoring system of claim 11, comprising a trained machine learning model to compute the MAP based on the plurality of features.

21. A method for monitoring mean arterial pressure (MAP) of a person based on PPG data comprising:
   arranging a first PPG sensor and second PPG sensor on a wrist of the person, wherein the second PPG sensor is spaced a fixed distance from the first PPG sensor;
   obtaining PPG data from the first PPG sensor and the second PPG sensor corresponding to blood flow in a vessel of the person;
   extracting a plurality of features from the PPG data and computing systolic velocity and diastolic velocity based on the plurality of features and the fixed distance; and
   computing the mean arterial pressure (MAP) based on the plurality of features, the systolic velocity, and the diastolic velocity.

22. The method of claim 21, further comprising sending the MAP to a portable computing device.

23. The method of claim 21, wherein computing the MAP is performed without use of ECG data.

24. The method of claim 21, further comprising computing diastolic blood pressure (DBP).

25. The method of claim 21, further comprising computing systolic blood pressure.

26. The method of claim 21, further comprising alerting the user to an optimal position on the wrist to strap the case thereto as the user adjusts and moves the case along the user's wrist.

27. The method of claim 21, wherein one of the plurality of features comprises: systolic volume, diastolic volume, diastolic distance, systolic distance, heart rate, diastolic time, and/or systolic time.

28. The method of claim 21, wherein the step of computing MAP is performed using a BP algorithm, and wherein the BP algorithm is calibrated using an ancillary BP measuring device, optionally a pressure cuff-type device.

29. The method of claim 28, wherein the computing MAP is performed compression-free subsequent to being calibrated.

30. The method of claim 28, wherein the computing MAP is performed continuously subsequent to being calibrated.

31. The method of claim 21, wherein the step of computing MAP is performed using a trained machine learning model for determining the MAP based on the plurality of features.

32. The method of claim 21, wherein the step of computing systolic velocity and diastolic velocity comprises identifying a first wave beginning and ending, a maximum peak as a systolic peak, and a diastolic peak as the highest peak to the right of the systolic peak, and measuring the time for each of the systolic peak and the diastolic peak to pass from the first location to the second location.

* * * * *